United States Patent [19]

Kirsch

[11] Plant 4,888

[45] Sep. 21, 1982

[54] LILY NAMED FELLOWSHIP

[75] Inventor: Ted T. Kirsch, Myrtle Point, Oreg.

[73] Assignee: Sun Valley Bulb Farms, Inc., Myrtle Point, Oreg.

[21] Appl. No.: 216,067

[22] Filed: Dec. 12, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—C. W. Rummler

[57] ABSTRACT

A new and distinct variety of Oriental hybrid lily of the Parkmannis type, particularly distinguished by a coral red band of coloring on the midrib of its generally pinkish white petals, which are borne in raceme arrangement on long, strong stems and stiff, outwardly-projecting pedicels, usually with one bud or flower on each pedicel; and by its emerald green, relatively disease-resistant foliage.

2 Drawing Figures

BACKGROUND OF THE PLANT

This new variety of lily plant originated as a seedling of unknown parentage growing among similar plants at my nursery in Arcata, Calif. Its delicately pastel colored, outward facing flowers and rich green foliage prompted me to asexually propagate this plant for study, with the result that I have found advantageous and distinctive characteristics in the new plant which make it a valuable addition to the field of commercial lily culture, particularly for cut flower production. Propagation of this new lily plant through successive generations at Arcata, Calif., by means of tissue culture and scales, has shown that its distinctive characteristics hold true from generation to generation and appear to be firmly fixed.

DESCRIPTION OF THE DRAWING

This new variety of lily plant is illustrated by the accompanying photographic drawing which, in full color, shows a full grown blooming plant in the upper view and a close-up view of a fully opened bloom in the lower view, the color rendition being as nearly true as can be obtained by conventional photographic procedures.

DESCRITPION OF THE NEW PLANT

The following is a detailed description of my new variety of lily based upon observations of field grown plants at Arcata, Calif., in the summer of 1980, the color designations being according to the R.H.S. Colour Chart published by The Royal Horticultural Society of London, England.

THE PLANT

Origin: Seedling.

Parentage: Unknown.

Classification: Oriental hybrid, Parkmannis type.

Form: Tall single stem from each bulb.

Height: About two to three and one-half feet at maturity.

Growth: Sturdy and upright, with excellent strength.

Cane size: Stems grow from about ¼ inch base diameter when the plant is at a height of two feet to ¾ inch base diameter when the plant is at a height of about three and one-half feet.

Foliage:

*Quantity.*—Abundant.

*Leaves at flower cluster.*—Three in number, one at the base of each pedicel about three and one-half inches long and one and one-half inches wide, and another on the pedicel approximately one inch from the flower bud and about two inches long and one-half inch wide.

*Shape.*—Ovate with cuspidate apex.

*Texture.*—Leathery.

*Aspect.*—Smooth.

*Ribs and veins.*—Distinct longitudinal veins from base to tip.

Stem bulblets (underground):

*Occurrence.*—One to three on each healthy, normal plant at digging time.

*Size.*—From ¼ inch to 1 inch in diameter.

*Color.*—White, with occasional pink shading at the tips.

Bulbs:

*Size.*—From 6 inches to 10 inches in circumference, depending on age.

*Color.*—White, with yellow and pink overtones. As the bulbs become larger and older, the overtones of yellow and pink become more and more prominent.

THE BUD

Form: Lanceolate, with acuminate apex.

Size: Averaging about 3½ to 4 inches long and ¾ inch to 1 inch in diameter.

Number: Usually one bud on each pedicel and up to fifteen buds on a plant stem according to culture and bulb size.

Opening rate: Normal, buds open successively from lowermost bud to the top bud, which is the last to open.

Color: Whitish pink at the tip of the bud, becoming a darker pink at the base when the sepals are about to divide and petals about to unfurl.

Surface texture: Rugose and leathery, with prominent veins.

Pedicel: Strong and generally upright, angled about 45° from the vertical.

*Color.*—Light green underneath and dark maroon on top; somewhat glabrous.

*Length.*—About 2 to 2½ inches.

THE FLOWER

Blooming habit: Annually, blooming profusely in July.

Size of flower: Medium, averaging about 4¼ to 6 inches in diameter.

Borne: The inflorescence of this plant has a raceme arrangement with each pedicel bearing one bud. The size of the bulb and its cultural care will determine the number of blooms and buds to be found on any given inflorescence. From large bulbs, this lily may have four to eight blooms open at one time.

Shape: Slightly cupped, uniformly spaced sepals and petals in star arrangement and with the very tips of the sepals and petals curving backwardly.

Petalage: Normal, three sepals and three petals.

*Form.*—Ovate with cuspidate apex and sinuate edges.

*Size.*—The petals are about 3 and ¾ inches long and 1 and ¾ inches wide.

*Color.*—Upper side: upon opening, the background color of the sepals and petals is a Whitish Pink, RHS 56D, and each petal has a Red midrib stripe of RHS 50A extending for two-thirds of the petal length. The margins of the midrib stripe and the outer portion of the stripe length fades to Red Purple, RHS 63B. The tip and the very outermost edge of the petal is white and the throat and center of the flower is lightly spotted with dark pinkish red spots. Under side: Red, RHS 56D, and somewhat glabrous.

*Papillae.*—Present on petals and from 4 to 8 in number.

*Texture.*—Leathery.

*Aspect.*—Velvety.

Fragrance: Sweet.

Discoloration: The color darkens somewhat as the bloom matures.

Effect of weather: Generally the flower is not affected by wet weather but ages as the temperature rises.

Persistence: The flower tends to hang on and dry.

Lasting quality:

*On the plant.*—Two to three weeks depending upon the size of the bulb and environmental temperature.

*As a cut flower.*—Ten days to two weeks.

REPRODUCTIVE ORGANS

Stamens:

*Anthers.*—Six in number and in orderly arrangement around the pistil. Length: about ¾ inch.

*Filaments.*—Length: about 2½ inches. Color: greenish yellow.

Pistils:

*Number.*—One.

*Style.*—Length — about 2¾ inches. Color: light green at the base, darkening somewhat at the stigma.

*Stigma.*—Light grey in color.

*Ovary.*—Classified as a schizocarp, about 2½ inches long and 1 inch in diameter, dehiscing into thirds and containing six rows of seeds of the usual shape for lilies.

I claim:

1. A new and distinct variety of Oriental hybrid lily plant, substantially as herein shown and described, characterized by its medium large, outwardly-facing, pinkish white flowers which are borne on strong, stiff, upwardly and outwardly-projecting pedicels; and by its generally white petals which are distinguished by a brilliant coral red midrib band appearing on a soft pink background surrounded by white undulating margins.

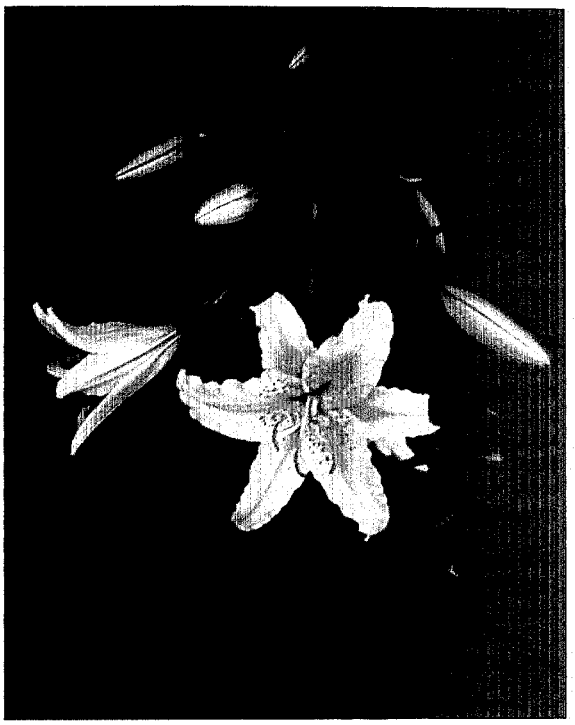
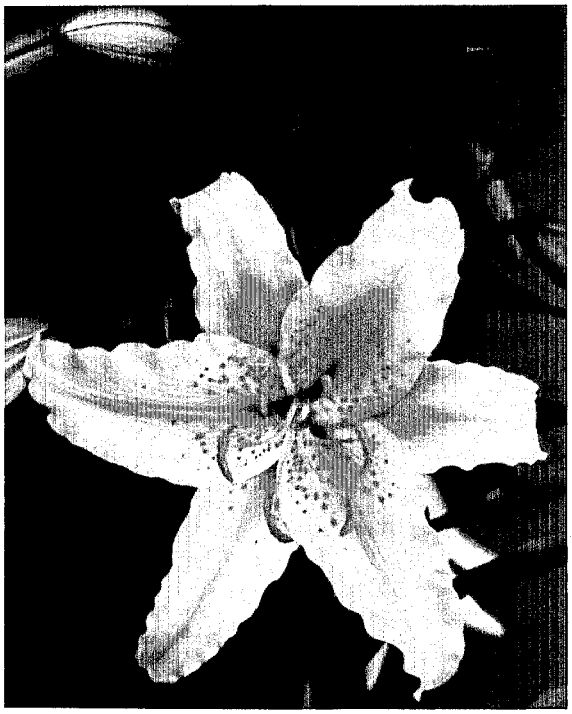

* * * * *